(12) United States Patent
Hutama et al.

(10) Patent No.: US 9,199,225 B2
(45) Date of Patent: Dec. 1, 2015

(54) METHOD FOR PREPARING METAL FLUORIDE CATALYSTS AND DEHYDROFLUORINATION METHOD USING THE SAME

(71) Applicant: Korean Institute of Science and Technology, Seoul (KR)

(72) Inventors: Hilman Hutama, Seoul (KR); Jeong-Myeong Ha, Seoul (KR); Chang Soo Kim, Daegu (KR); Hong Gon Kim, Seoul (KR); Jae Wook Choi, Incheon (KR); Dong Jin Suh, Seoul (KR); Hyun Joo Lee, Gwangmyeong (KR); Byoung Sung Ahn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/475,923

(22) Filed: Sep. 3, 2014

(65) Prior Publication Data

US 2015/0080617 A1 Mar. 19, 2015

(30) Foreign Application Priority Data

Sep. 17, 2013 (KR) .................. 10-2013-0111959

(51) Int. Cl.
*B01J 27/132* (2006.01)
*B01J 37/26* (2006.01)
*B01J 27/12* (2006.01)
*C07C 17/25* (2006.01)

(52) U.S. Cl.
CPC ............. *B01J 27/132* (2013.01); *B01J 27/12* (2013.01); *B01J 37/26* (2013.01); *C07C 17/25* (2013.01)

(58) Field of Classification Search
CPC ............................ C07C 17/23; B01J 27/132
USPC .......................................... 570/156; 423/472
See application file for complete search history.

(56) References Cited

U.S. PATENT DOCUMENTS

| 7,674,939 | B2 | 3/2010 | Mukhopadhyay et al. |
| 7,786,333 | B2 | 8/2010 | Van Der Puy et al. |
| 7,851,402 | B2 * | 12/2010 | Cunningham et al. ........ 502/308 |
| 8,221,902 | B2 | 7/2012 | Grosso et al. |
| 2010/0004492 | A1 | 1/2010 | Nappa et al. |
| 2013/0060069 | A1 | 3/2013 | Elsheikh et al. |

FOREIGN PATENT DOCUMENTS

| JP | 2009-542812 A | 12/2009 |
| KR | 10-0107273 B1 | 8/1996 |
| KR | 10-2009-0112593 | 10/2009 |
| KR | 10-2013-0079655 | 7/2013 |
| WO | 2008-008350 A2 | 1/2008 |
| WO | WO 2009-138764 A1 | 11/2009 |

OTHER PUBLICATIONS

Noack et al, Dalton Transactions, 2013, 42(16), 5706-10.*
Fritz et al, Dalton Transactions., 2012, 41(37), 11351-60.*
Katharina Teinz et al., "Highly selective metal fluoride catalysts for the de hydrohalogenation of 3-chloro-1,1,1,3-tetrafluorobutane", Journal of Catalysis, 2011, vol. 282, pp. 175-182.
Stephan Rüdiger et al., "The fluorlytic sol-gel route to metal fluorides—a versatile process opening a variety of application fields", Dalton Transactions, 2008, vol. 7, No. 9, pp. 1117-1127.

* cited by examiner

*Primary Examiner* — Shailendra Kumar
(74) *Attorney, Agent, or Firm* — Goldilocks Zone IP Law

(57) ABSTRACT

Disclosed is a method for preparing a metal fluoride catalyst as a dehydrofluorination catalyst having high activity under a mild condition using a trifluoroacetic acid solution with no use of HF gas having fluidity and corrosive property. Disclosed also is a dehydrofluorination method for preparing HFO-1225ye from HFP-236ea by using the catalyst with high efficiency.

6 Claims, 2 Drawing Sheets

METHOD FOR PREPARING METAL FLUORIDE CATALYSTS AND DEHYDROFLUORINATION METHOD USING THE SAME

CROSS-REFERENCE TO RELATED APPLICATION

This application claims priority to Korean Patent Application No. 10-2013-0111959, filed on Sep. 17, 2013, and all the benefits accruing therefrom under 35 U.S.C. §119, the contents of which in its entirety are herein incorporated by reference.

DESCRIPTION ABOUT NATIONAL RESEARCH AND DEVELOPMENT SUPPORT

This study was supported by the Alternate Material Commercialization R&D Project of Ministry of Trade, Industry & Energy, Republic of Korea (Korea Evaluation Institute of Industrial Technology, Project No. 10040765, Development of HFO-1234yf manufacturing method) under the superintendence of Korea Institute of Science and Technology.

BACKGROUND

1. Field

The present disclosure relates to a method for preparing a metal fluoride catalyst and dehydrofluorination method using the same. More particularly, the present disclosure relates to a method for preparing a metal fluoride catalyst, including reacting a chromium precursor as a metal precursor with a trifluoroacetic acid solution to form a chromium fluoride ($Cr(NO_3)_3 \cdot 9H_2O$) catalyst, and then reacting the resultant catalyst with 1,1,2,3,3,3-hexafluoropropane (also referred to as HFP-236ea hereinafter) to obtain 1,2,3,3,3-pentafluoropropene (also referred to as HFO-1225ye hereinafter), as well as to a dehydrofluorination method using the same.

2. Description of the Related Art

It is known that 1,1,1,2-tetrafluoroethane (also referred to as HFC-134a hereinafter) used as a refrigerant for cars is a greenhouse gas showing a global warming index up to 1300 times of the global warming index of carbon dioxide despite its high refrigerant characteristics.

Thus, EU prohibits the use of HFC-134a and regulates that a refrigerant for cars produced after 2011 cannot have a global warming index of 150 or higher. It is expected that such a regulation is extended to all cars in EU in 2017.

Under these circumstances, 2,3,3,3-tetrafluoropropene (also referred to as HFO-1234yf hereinafter) is a very suitable refrigerant and has a global warming index corresponding to about 4. It is also known that HFO-1234yf is produced by allowing the starting material, 1,1,2,3,3,3-hexafluoropropene (also referred to as HFP hereinafter) to pass through hydrogenation and dehydrofluorination alternately (U.S. Pat. No. 7,985,884 B2) (see the following Chemical Formula 1).

[Chemical Formula 1]

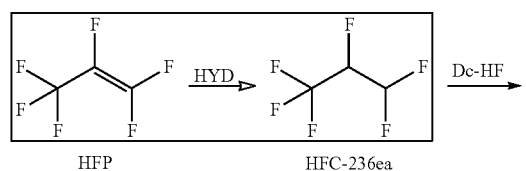

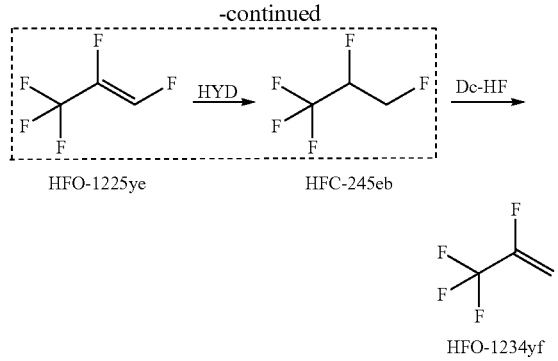

When preparing HFO-1234yf as shown in the above chemical formula, dehydrofluorination is essentially required as an intermediate process and a catalyst used for the dehydrofluorination according to the related art is a metal oxide catalyst treated with hydrofluoric acid (HF).

However, use of the HF-treated metal oxide catalyst entails such problems as corrosion of a reactor caused by HF during the preparation of catalyst, a decrease in active spots of a catalyst caused by treatment with HF, difficulty in forming a catalyst due to the use of HF, or the like.

Therefore, to solve the above-mentioned problems, the present inventors have found a method for preparing a metal fluoride catalyst as a substitute for the method for preparing a metal oxide catalyst including treatment with HF according to the related art, as well as a dehydrofluorination method using the same.

REFERENCES

Patent Documents

US Patent Publication No. U.S. Pat. No. 7,786,333B
US Patent Publication No. IS 7,674,939B2

Non-Patent Documents

Kemnitz et al., J. Catal. 2011, 282, 175.

SUMMARY

The present disclosure is directed to providing a method for preparing a metal fluoride catalyst as a substitute for the method for preparing a metal oxide catalyst including treatment with HF according to the related art. The present disclosure is also directed to providing a dehydrofluorination method including forming 1,2,3,3,3-pentafluoropene (also referred to as HFO-1225ye hereinafter) from 1,1,2,3,3,3-hexafluoropropane (HFP-236ea) used as a refrigerant or raw material thereof with high yield and high selectivity by using the metal fluoride catalyst.

In one aspect, there is provided a method for preparing a metal fluoride catalyst including adding a trifluoroacetic acid solution to a metal precursor to form a metal fluoride catalyst.

According to an embodiment, the metal precursor may be a chromium precursor.

According to another embodiment, the chromium precursor may be chromium oxide obtained by a sol-gel process.

According to still another embodiment, the chromium precursor may be in the form of wet gel.

According to still another embodiment, the trifluoroacetic acid solution may be a solution of trifluoroacetic acid dissolved in water, ethanol or dioxane.

According to yet another embodiment, the trifluoroacetic acid solution may have a concentration of 0.001-0.1 M.

In another aspect, there is provided a metal fluoride catalyst obtained by the above-described method. According to an embodiment, the metal fluoride catalyst may be a chromium fluoride catalyst.

In still another aspect, there is provided a dehydrofluorination method including: introducing HFP-236ea into a reactor; and adding the metal fluoride catalyst obtained by the above-described method to the reactor to obtain HFO-1225ye.

According to an embodiment, when preparing HFO-1225ye, the reactor may have a temperature of 300-500° C.

According to another embodiment, the metal fluoride catalyst added to the reactor may be a chromium fluoride catalyst.

According to the method for preparing a metal fluoride catalyst disclosed herein, it is possible to obtain a metal fluoride as a dehydrofluorination catalyst having high activity under a mild condition using a trifluoroacetic acid solution with no use of HF gas having fluidity and corrosive property.

In addition, the metal fluoride, particularly a chromium fluoride catalyst, obtained as a highly active dehydrofluorination catalyst according to the above-described method may be used to produce HFO-1225ye, an intermediate for preparing an environmentally friendly refrigerant HFO-1234yf, continuously with high efficiency.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION OF MAIN ELEMENTS

Figure 1:
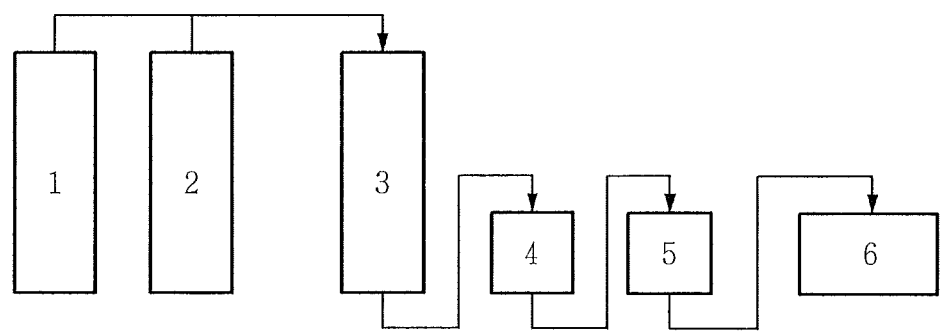
FIG. 1 is a schematic view showing a reaction system for dehydrofluorination of HFC-236ea using a gas-phase reactor according to an embodiment.

1: high-pressure cylinder for HFC-236ea
2: high-pressure cylinder for nitrogen
3: continuous gas-phase reactor
4: water trap
5: silica gel trap
6: GC-FID

DETAILED DESCRIPTION

Exemplary embodiments now will be described more fully hereinafter with reference to the accompanying drawings, in which exemplary embodiments are shown.

Preparation of Metal Fluoride Catalyst

In one aspect, there is provided a method for preparing a metal fluoride catalyst, including adding a trifluoroacetic acid solution to a metal precursor to obtain a metal fluoride catalyst.

There is no particular limitation in the metal catalyst, as long as it is a precursor material of the metal fluoride catalyst capable of functioning as a catalyst for dehydrofluorination of HFP-236ea.

According to an embodiment, the metal precursor may be a chromium precursor, and the chromium precursor may be a chromium oxide obtained by a sol-gel process.

According to another embodiment, the chromium oxide may be in the form of wet gel obtained by a sol-gel process. When using such a wet gel-type chromium oxide as a chromium precursor, the resultant metal fluoride catalyst, i.e., chromium fluoride ($CrO_xF_y$) catalyst shows excellent reaction activity.

According to an embodiment, the chromium precursor may be cobalt-colored chromium oxide gel obtained by dissolving chromium (III) nitrate nona-hydrate ($Cr(NO_3)_3 \cdot H_2O$) into ethanol and adding propylene oxide thereto.

There is no particular limitation in the trifluoroacetic acid (TFA) solution, as long as it is capable of reacting with the metal precursor to form a metal fluoride. For example, the TFA solution may be a solution of trifluoroacetic acid dissolved in water, ethanol or dioxane.

According to an embodiment, when a wet gel-type chromium fluoride ($CrO_xF_y$) is prepared through the above procedure, it may be washed with ethanol or ion exchange water, followed by firing, to provide a catalyst.

The method and the metal fluoride catalyst, particularly chromium fluoride catalyst obtained by the method are not based on the use of hydrofluoric acid (HF), which, otherwise, is used for treating a metal oxide catalyst according to the related art. As a result, it is possible to prevent the corrosion of a reactor during the preparation of a catalyst, to avoid such problems as a decrease in active spots of a catalyst caused by treatment with HF and difficulty in forming a catalyst due to the use of HF, and to obtain a highly active dehydrofluorination catalyst efficiently.

Dehydrofluorination

The metal fluoride catalyst for dehydrofluorination obtained as described above is used to obtain HFO-1225ye generated as an intermediate product during the preparation of the final refrigerant, HFO-1234yf, from HFC-236ea.

This is a dehydrofluorination process using the metal fluoride catalyst obtained as described above.

First, 1,1,2,3,3,3-hexafluoroproane (HFP-236ea) is introduced to a reactor.

After introducing HFP-236ea, the metal fluoride catalyst is added to the reactor. According to an embodiment, the metal fluoride catalyst added to the reactor may be a chromium fluoride.

Addition of the metal fluoride catalyst to HFP-236ea in the reactor results in progress of dehydrofluorination simultaneously with formation of double bonds.

Although there is no particular limitation in the reactor, the reactor may be a gas-phase reactor operated at high temperature or a continuous reactor amenable to mass production.

Herein, the temperature condition in the reactor is not particularly limited but may be 300-500° C., for example.

Herein, the pressure condition in the reactor is not particularly limited but may be an ambient pressure condition, for example.

The process of dehydrofluorination including the above procedure is not based on the use of hydrofluoric acid but uses a metal fluoride catalyst that is a highly active dehydrofluorination catalyst obtained with no use of hydrofluoric acid. Thus, it is possible to produce HFO-1225ye generated as an intermediated product during the preparation of HFO-1234yf expected as an environmentally friendly refrigerant, with high efficiency continuously.

EXAMPLES

The examples and experiments will now be described. The following examples and experiments are for illustrative purposes only and not intended to limit the scope of the present disclosure.

Examples 1, 2 and 3 (Preparation of Chromium Fluoride ($CrO_xF_y$) Using TFA)

First, 0.65 g of chromium (III) nitrate nona-hydrate ($Cr(NO_3)_3 9H_2O$) as a Cr precursor is dissolved into 2.5 mL of ethanol, 1.0 g of propylene oxide is added thereto, and the reaction mixture is allowed to stand for up to 4 hours to obtain cobalt-colored wet gel of chromium oxide.

The resultant wet gel of chromium oxide is mixed with 2 mL of 0.001 M (Example 1), 0.01 M (Example 2) or 0.1 M (Example 3) aqueous trifluoroacetic acid solution and treated at room temperature under ambient pressure for 12 hours without stirring.

The chromium oxide gel treated with trifluoroacetic acid as described above is washed with ethanol, vacuum dried at 90° C. for 12 hours, and fired at 500° C. under air for 3 hours to obtain a chrome fluoride ($CrO_xF_y$) catalyst.

Comparative Example 1 (Preparation of Chrome Fluoride ($CrO_xF_y$) Using HF)

First, 0.65 g of chromium (III) nitrate nona-hydrate ($Cr(NO_3)_3 9H_2O$) as a Cr precursor is dissolved into 2.5 mL of ethanol, 1.0 g of propylene oxide is added thereto, and the reaction mixture is allowed to stand for up to 4 hours to obtain cobalt-colored wet gel of chromium oxide.

The resultant wet gel of chromium oxide is mixed with 2 mL of aqueous hydrofluoric acid (HF) solution containing 0.01 M HF dissolved therein and treated at room temperature under ambient pressure for up to 4 hours without stirring.

The gel treated with HF as described above is washed with ion exchange water and fired at 500° C. under air for 3 hours to obtain a chrome fluoride ($CrO_xF_y$) catalyst.

Test Examples (Dehydrofluorination Using Chrome Fluoride ($CrO_xF_y$) Catalyst of Example 1)

To carry out dehydrofluorination of HFC-236ea, 0.107 mL of the chrome fluoride catalyst is introduced to a reactor so that the gas hourly space velocity (GHSV) may be 3375 $h^{-1}$ during the reaction, and then a reaction mixture including 4 mL/min of nitrogen and 2 mL/min of HFC-236ea is allowed to flow through a ¼ inch tubular reactor. The temperature of the reactor is maintained at 400° C. during the reaction.

The reaction product passed through the reactor is allowed to pass through a water trap to remove hydrofluoric acid (HF) produced during the reaction, and through a silica gel trap to remove water vapor remaining in a gas phase.

Figure 2:
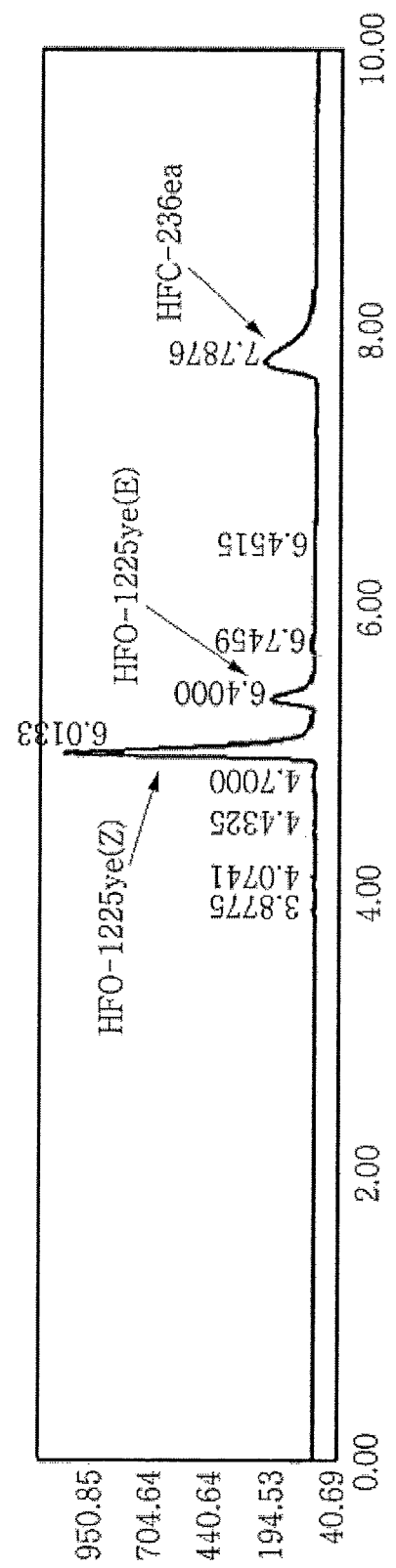
FIG. 2 shows the results of gas chromatography analysis of the metal fluoride catalyst according to an embodiment.

Then, the reaction product (HFO-1225ye) is analyzed by a gas chromatography system (see FIG. 2).

Test Example 1

Each of the chromium fluoride ($CrO_xF_y$) catalysts obtained from Examples 1, 2 and 3 is introduced to a continuous type gas phase reactor to carry out dehydrofluorination (supra) of HFC-236ea. The results are shown in the following Table 1.

TABLE 1

| Test conditions | Example 1 | Example 2 | Example 3 |
|---|---|---|---|
| Catalyst | $CrO_xF_y$ catalyst obtained by using TFA (TFA 0.001M) | $CrO_xF_y$ catalyst obtained by using TFA (TFA 0.01M) | $CrO_xF_y$ catalyst obtained by using TFA (TFA 0.1M) |
| Flow of HFC-236ea (mL/min) | 2 | 2 | 2 |
| Volume of catalyst (mL) | 0.107 | 0.107 | 0.107 |
| Flow of $N_2$ (mL/min) | 4 | 4 | 4 |
| Reaction temperature (° C.) | 400 | 400 | 400 |
| Reaction pressure (bar) | 1 | 1 | 1 |
| Conversion (%) of HFC-236ea | 75.1 | 85.8 | 44.6 |
| Selectivity (%) of HFO-1225ye | 100 | 100 | 100 |

It can be seen from the above results that when using the chrome fluoride ($CrO_xF_y$) catalyst (Example 2) obtained by using 0.01 M aqueous TFA solution, 85.8% or less of HFC-236ea is converted into HFO-1225ye completely and selectively.

Test Example 2

The chromium fluoride ($CrO_xF_y$) catalysts obtained from Comparative Example 1 is used to carry out dehydrofluorination (supra) of HFC-236ea while controlling the reaction temperature in a continuous type gas-phase reactor. The results are shown in the following Table 2.

TABLE 2

| Test conditions | Comparative Example 1 |
|---|---|
| Catalyst | $CrO_xF_y$ catalyst obtained by using HF, 0.107 mL |
| Flow of HFC-236ea (mL/min) | 2 |
| Flow of $N_2$ (mL/min) | 4 |
| Reaction temperature (° C.) | 400 |
| Reaction pressure (bar) | 1 |
| Conversion (%) of HFC-236ea | 32.5 |
| Selectivity (%) of HFO-1225ye | 100 |

It can be seen from the above results that when using the chrome fluoride ($CrO_xF_y$) catalyst obtained by using hydrofluoric acid (HF), at most 32.5% of HFC-236ea is converted into HFO-1225ye completely and selectively.

Test Example 3

Commercially available $Cr_2O_3$ powdery catalyst is used to carry out dehydrofluorination (supra) of HFC-236ea while controlling the reaction temperature in a continuous type gas phase reactor. The results are shown in the following Table 3.

TABLE 3

| Test conditions | Comparative Example 2 |
|---|---|
| Catalyst | Commercially available $Cr_2O_3$ powdery catalyst, 0.107 mL |
| Flow of HFC-236ea (mL/min) | 2 |
| Flow of $N_2$ (mL/min) | 4 |
| Reaction temperature (° C.) | 400 |

TABLE 3-continued

| Test conditions | Comparative Example 2 |
| --- | --- |
| Reaction pressure (bar) | 1 |
| Conversion (%) of HFC-236ea | 0 |
| Selectivity (%) of HFO-1225ye | — |

It can be seen from the above results that when using $Cr_2O_3$ powdery catalyst, no HFC-236ea is converted.

Test Example 4

Commercially available $CrF_3$ powdery catalyst is used to carry out dehydrofluorination (supra) of HFC-236ea while controlling the reaction temperature in a continuous type gas phase reactor. The results are shown in the following Table 4.

TABLE 4

| Test conditions | Comparative Example 3 |
| --- | --- |
| Catalyst | Commercially available $CrF_3$ powdery catalyst, 0.107 mL |
| Flow of HFC-236ea (mL/min) | 2 |
| Flow of $N_2$ (mL/min) | 4 |
| Reaction temperature (° C.) | 400 |
| Reaction pressure (bar) | 1 |
| Conversion (%) of HFC-236ea | 0 |
| Selectivity (%) of HFO-1225ye | — |

It can be seen from the above results that when using $CrF_3$ powdery catalyst, no HFC-236ea is converted.

While the exemplary embodiments have been shown and described, it will be understood by those skilled in the art that various changes in form and details may be made thereto without departing from the spirit and scope of the present disclosure as defined by the appended claims.

What is claimed is:

1. A method for preparing a metal fluoride catalyst, comprising adding a trifluoroacetic acid solution to a metal precursor to form a metal fluoride catalyst,
    wherein the metal precursor is a chromium oxide wet gel obtained by a sol-gel process; and
    wherein the trifluoroacetic acid solution has a concentration of 0.001-0.1M.

2. The method for preparing a metal fluoride catalyst according to claim 1, wherein the trifluoroacetic acid solution is a solution of trifluoroacetic acid dissolved in water, ethanol or dioxane.

3. A dehydrofluorination method comprising:
    introducing 1,1,2,3,3,3-hexafluoropropane into a reactor; and
    adding the metal fluoride catalyst obtained by the method as defined in claim 1 to the reactor to obtain 1,2,3,3,3-pentafluoropropene.

4. The dehydrofluorination method according to claim 3, wherein the reactor has a temperature of 300-500° C. when preparing 1,2,3,3,3-pentafluoropropene.

5. The dehydrofluorination method according to claim 3, wherein the metal fluoride catalyst is a chromium fluoride catalyst.

6. The method of preparing a metal fluoride catalyst according to claim 1, wherein the metal fluoride catalyst is defined by Formula 1:
    $CrO_xF_y$, wherein x and y are integers greater than 0.

* * * * *